United States Patent
Lee et al.

(10) Patent No.: US 11,549,946 B2
(45) Date of Patent: Jan. 10, 2023

(54) METHOD FOR DETECTING CHOLANGIOCARCINOMA CELLS

(71) Applicants: National Tsing Hua University, Hsinchu (TW); ACADEMIA SINICA, Taipei (TW)

(72) Inventors: Gwo Bin Lee, Hsinchu (TW); Shang-Cheng Hung, Taipei (TW); Wei-Chun Tsai, Hsinchu (TW)

(73) Assignees: NATIONAL TSING HUA UNIVERSITY, Hsinchu (TW); ACADEMIA SINICA, Taipei (TW)

( * ) Notice: Subject to any disclaimer, the term of this patent is extended or adjusted under 35 U.S.C. 154(b) by 80 days.

(21) Appl. No.: 16/516,475

(22) Filed: Jul. 19, 2019

(65) Prior Publication Data
US 2020/0355692 A1   Nov. 12, 2020

(30) Foreign Application Priority Data
May 10, 2019   (TW) .................. 108116267

(51) Int. Cl.
*G01N 33/574* (2006.01)
*B01L 9/00* (2006.01)
*G01N 33/543* (2006.01)

(52) U.S. Cl.
CPC ........ *G01N 33/57438* (2013.01); *B01L 9/527* (2013.01); *G01N 33/54326* (2013.01)

(58) Field of Classification Search
CPC ....... G01N 33/57438; G01N 33/54326; G01N 2400/38; B01L 9/527; B01L 3/5027; B01F 13/0059; B01F 11/0045
See application file for complete search history.

(56) References Cited

U.S. PATENT DOCUMENTS

2021/0046479 A1* 2/2021 Hung ............... G01N 33/57407

OTHER PUBLICATIONS

Hung et al. A microfluidic chip for detecting cholangiocarcinoma cells in human bile. Scientific Reports, 2017, vol. 7, No. 4248, pp. 1-10. (Year: 2017).*
Tsai et al. Proceedings of the 12th IEEE International Conference on Nano/Micro Engineered and Molecular Systems, 2017, Los Angeles, USA, pp. 489-493. (Year: 2017).*
Tsai et al. An integrated microfluidic system for the isolation and detection of ovarian circulating tumor cells using cell selection and enrichment methods. Biomicrofluidics 2017, 11(3): 034122, pp. 1-11. (Year: 2017).*
Gopinathan et al. Automated selection of aptamers against cholangiocarcinoma cells on an intergrated microfluidic platform. Biomicrofluidics 2017, vol. 11, Issue 4:044101, pp. 1-15 (Year: 2017).*

* cited by examiner

*Primary Examiner* — Shafiqul Haq
(74) *Attorney, Agent, or Firm* — WPAT, PC

(57) ABSTRACT

The present disclosure provides a method for detecting cholangiocarcinoma cells. The capture rate of the cholangiocarcinoma cells of the present disclosure is higher than 70%, and a plurality of octasaccharides with high affinity and specificity can be modified on the surface of magnetic beads to capture and analyze cholangiocarcinoma cells under test, wherein the cholangiocarcinoma cells can be circulating tumor cells in cholangiocarcinoma.

6 Claims, 10 Drawing Sheets

METHOD FOR DETECTING CHOLANGIOCARCINOMA CELLS

CROSS-REFERENCE TO RELATED APPLICATION

This application claims priority of Taiwan patent application No. 108116267, filed on May 10, 2019, the content of which is incorporated herein in its entirety by reference.

BACKGROUND OF THE INVENTION

1. Field of the Invention

The present invention relates to a method for detecting cholangiocarcinoma cells.

2. The Prior Art

Cancer, or malignant tumor, causes millions of deaths each year worldwide, and it is also the number one cause of death in Taiwan in recent years. Among various cancers, cholangiocarcinoma is a rare primary malignant liver tumor, and its clinical symptoms, diagnosis and epidemiological characteristics are all different from those of another primary malignant liver tumor hepatocellular carcinoma. The biliary system is distributed throughout the liver, starting from the bile capillarys formed by the groove on the surface of the hepatic cells, gradually converging into a small bile duct, the left and right intrahepatic bile ducts and then passing throughout the liver to synthesize a common hepatic duct, becoming a common bile duct after meeting the gallbladder, and finally flowing into the duodenum. Cholangiocarcinoma can be produced from any place with bile ducts, including intrahepatic bile ducts and extrahepatic bile ducts. Cholangiocarcinoma is divided into two types: hepatic portal type and peripheral type. The former may cause obstructive jaundice even if the tumor is small. The latter often forms a lesion in the liver like liver cancer to occupy part of the liver, and there are no symptoms of jaundice until the end stage. Regardless of the type of cholangiocarcinoma, the prognosis is very bad.

Because there are no obvious symptoms in cholangiocarcinoma in the early stage, it is difficult to diagnose and detect. While most patients are diagnosed with cholangiocarcinoma, the disease has progressed to the advanced stage and cannot be cured. Relief care can be performed in these incurable patients, including surgical resection, chemotherapy, radiation therapy, and placement of biliary stents. Complete surgical resection is the only hope for cure, but about one-third of patients have tumors that invade the common bile duct, and such tumors cannot be surgically removed, so only a few tumors can be completely resected. Chemotherapy and radiation therapy are still recommended after complete resection. Some patients who meet certain conditions can undergo liver transplantation, but the five-year survival rate after surgery is still less than 50%. Therefore, researchers in the field are committed to the development of new treatment and detection methods for cholangiocarcinoma in order to achieve the goal for early detection and early treatment.

Cancer metastasis is the leading cause of death induced by cancer. Circulating tumor cells (CTCs), which have been confirmed since 1869, are cells that escape from the primary tumor site to the adjacent vasculature and subsequently present in the blood circulation. There is evidence that the presence of circulating tumor cells in the blood circulation is associated with cancer metastasis. Therefore, those skilled in the art have focused on studying circulating tumor cells to understand the mechanism of cancer metastasis. This research direction can stimulate the skilled artisan to develop new cancer treatment strategies.

In addition, in clinical applications, analysis of circulating tumor cells (considered as liquid tumor biopsy) can be used as a diagnostic or prognostic tool for monitoring cancer metastasis or therapeutic response, and guiding individualization treatment. In order to achieve these goals, it is necessary to isolate circulating tumor cells with high purity from blood samples to avoid as much as possible analysis interference caused by peripheral blood cells (mainly white blood cells).

However, circulating tumor cells are very rare in blood samples at a concentration of approximately one circulating tumor cell per $10^5$ to $10^7$ blood mononuclear cells. This phenomenon makes it difficult to isolate and purify circulating tumor cells, particularly in a high purity manner. At present, there are various methods for isolating and purifying circulating tumor cells, which can be roughly classified into physical and biochemical methods. In general, the physical method for isolating circulating tumor cells (primarily filtration) is easy to perform and does not require labeling of harvested cells, but the purity of the cells is lower than that of the biochemical methods. In the biochemical methods, the immune cell isolation method (such as the method of immunomagnetic beads) is mainly used for the isolation and purification of circulating tumor cells. In this method, magnetic beads coupled to specific antibodies of surface biomarkers (mainly epithelial cell adhesion molecule (EpCAM) and cytokeratins (CKs)) of circulating tumor cells are commonly used for identifying and binding to circulating tumor cells. Magnetically labeled circulating tumor cells are isolated from peripheral cells by an applied magnetic field. Circulating tumor cell isolation according to this method is primarily used in current circulating tumor cell isolation or detection systems (e.g., CellSearch™ system, magnetically activated cell sorting system, or Dynabeads™). In general, the cell purity of circulating tumor cells obtained by the above cell isolating method ranges from 20% to 50%.

Although the above-described methods for detecting and isolating circulating tumor cells have been present, the white blood cell contamination in the obtained circulating tumor cells is often unavoidable. Problems may be caused in subsequent analysis of circulating tumor cells (especially gene expression analysis), which may cause underestimation or misjudgment. The problem is mainly because the expression level of some white blood cell related genes is still unclear. Therefore, the presence of these white blood cells can interfere with subsequent analysis. This fact highlights the importance of isolating circulating tumor cells with high purity (ideally 100%) for subsequent high precision analysis. In addition to the purity of circulating tumor cells, there are some important biological issues that are needed for further consideration. As mentioned above, most of the methods for isolating or purifying circulating tumor cells rely primarily on the use of EpCAM or CKs to identify circulating tumor cells. However, circulating tumor cells (especially circulating tumor cells with high metastatic potential) may undergo epithelial-to-mesenchymal transition (EMT). After that, circulating tumor cells may reduce the expression of EpCAM and CKs and become moving cells to distant metastatic sites. In this regard, if a conventional method for isolating and detecting circulating tumor cells is used, these circulating tumor cells that are clinically associated with cancer metastasis may be missed, especially the circulating tumor cells in cholangiocarcinoma difficult to detect.

Therefore, those skilled in the art are in urgent need of developing novel methods for detecting cholangiocarcinoma cells (e.g., circulating tumor cells in cholangiocarcinoma) to overcome the disadvantages of the prior art and to benefit a large group of people in need thereof.

SUMMARY OF THE INVENTION

A primary objective of the present invention is to provide a method for detecting cholangiocarcinoma cells, comprising the following steps: (a) contacting a sample with at least one octasaccharide to bind the cholangiocarcinoma cells in the sample to the at least one octasaccharide; and (b) detecting the presence of the cholangiocarcinoma cells in the sample by a binding reaction.

According to an embodiment of the present invention, in step (a), the method further comprises modifying a surface of a magnetic bead with the at least one octasaccharide.

According to an embodiment of the present invention, the binding reaction is performed by the magnetic bead modified with the at least one octasaccharide to capture the cholangiocarcinoma cells, and the cholangiocarcinoma cells bound to the at least one octasaccharide are isolated via a magnetic field.

According to an embodiment of the present invention, the at least one octasaccharide is attached to a detectable label, and the detectable label is selected from the group consisting of a fluorescent label, a chemiluminescent label, a radioisotope, an enzyme label, and a biotin.

According to an embodiment of the present invention, in step (b), the method further comprises performing an immunofluorescence staining on the cholangiocarcinoma cells bound to the at least one octasaccharide.

According to an embodiment of the present invention, the cholangiocarcinoma cells are circulating tumor cells in cholangiocarcinoma.

According to an embodiment of the present invention, the immunofluorescence staining is performed using a cytokeratin 17 (CK17) antibody and a CD45 antibody, and the circulating tumor cells in cholangiocarcinoma are CK17-positive and CD45-negative cells.

According to an embodiment of the present invention, the method is performed on a microfluidic chip, wherein the microfluidic chip comprises an operating condition applying a gauge pressure ranging from −100 to −400 mmHg at a driving frequency of 4 Hz.

According to an embodiment of the present invention, the at least one octasaccharide has a structural formula (I):

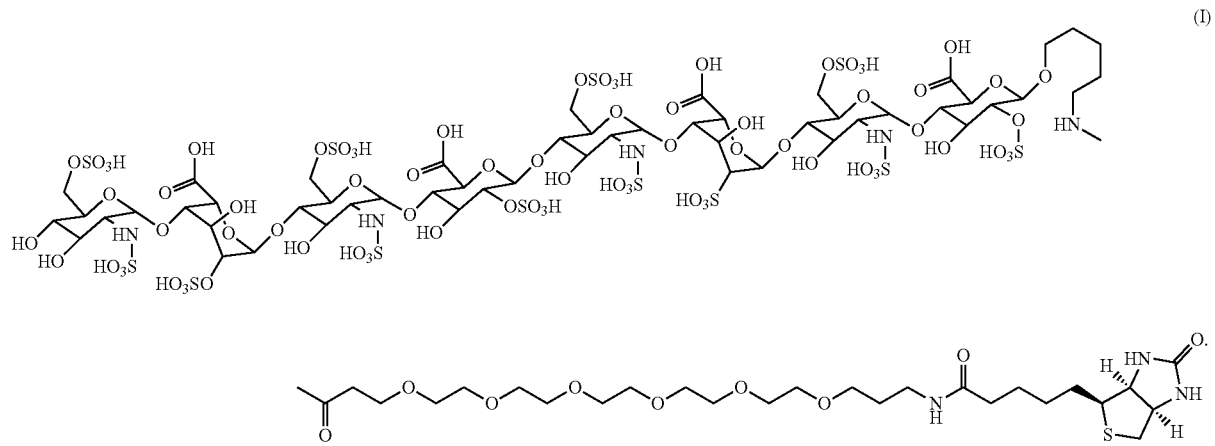

According to an embodiment of the present invention, the at least one octasaccharide has a structural formula (II):

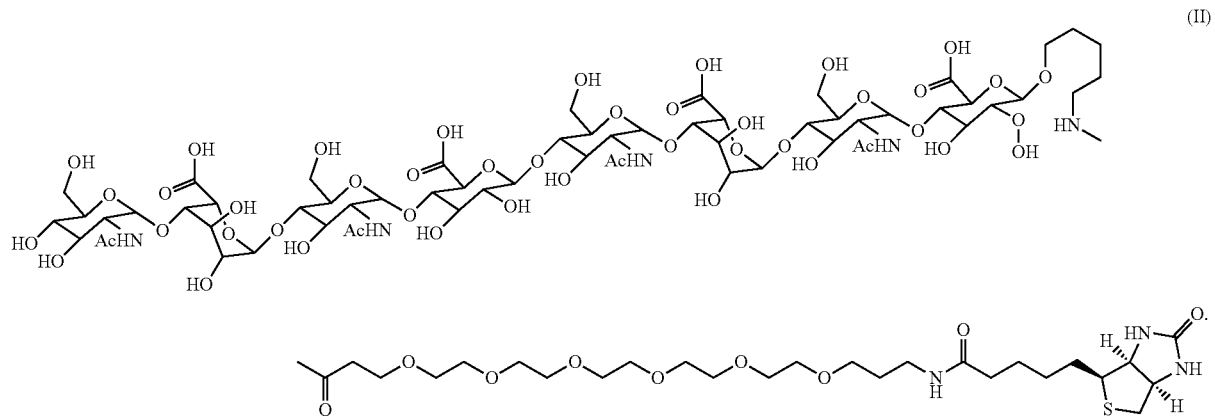

According to an embodiment of the present invention, the sample is a whole blood from a subject, and the whole blood is subjected to a pretreatment for removing red blood cells and white blood cells.

In summary, the method of the invention has the following effects: the capture rate of cholangiocarcinoma cells is higher than 70%, and the method comprises modifying a surface of a magnetic bead with a variety of octasaccharides with high affinity and specificity to capture and analyze CTCs under test. In addition, compared with the conventional mixer, the method of the invention can reduce the mixing time of the sample to be tested and the specific magnetic beads from 30 minutes to 5 minutes using the microfluidic chip. Through a complete set of the detection process, cholangiocarcinoma cells can be successfully captured for specific fluorescent signals of cholangiocarcinoma showing Hoechst 33258 and cytokeratin 17 (CK17) without anti-CD45 to exclude interference from white blood cells and other cells. Furthermore, compared to the detection time of a conventional CellSearch® machine, the detection time can be reduced to two hours via the application of the microfluidic chip system. The present invention further utilizes a preliminary test outside the chip on a clinical sample, and successfully detects 1 and 4 cholangiocarcinoma cells in 3 mL of blood in two intrahepatic cholangiocarcinoma patients. That is, compared with the prior art, the whole blood volume required by the present invention is only 2-3 mL for the detection of cholangiocarcinoma cells, and the prior art requires at least 7.5 mL of whole blood volume. Therefore, the technical feature of the present invention is to successfully develop an integrated microfluidic system as a method for detecting circulating tumor cells in a small amount for the first time.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of 20%, preferably within ±10%, and most preferably within +5%.

As used herein, the term "circulating tumor cell (CTC)" is intended to encompass any rare tumor cell present in a biological sample associated with cancer.

The terms of "microfluidic chip" and "chip" are exchangeable in the present specification, which indicates an independent integrated unit having a microfluidic reactor, one or more microfluidic channels, and one or more valves. The microfluidic chip also encompasses typical elements, such as pumps, chambers, mixers, and the like. In general, the microfluidic chip is made of elastomer, glass or silicon. Typically, the microfluidic chip is a box having height less than the length and the width thereof. Therefore, the shape of chip can be, but not limited to, cube or cylinder.

The term of "sample" in the present specification indicates the specimens collected from patients. The sample comprises but not limited to body fluids, such as blood, serums, plasma, urine, saliva, tears, pharyngeal epithelial cells, cerebrospinal fluids, lymph, dialysates, lavage fluids, and fluids derived from cells or tissues. The term of "sample" also indicates cells and ones derived therefrom, including cells in culture, the supernatant of the cell culture, and cell debris. In addition, the term of "sample" indicates the fluids derived from organs and tissue cultures, tissue biopsies, tumor biopsies, fecal sample, fluids extracted from tissues and cells isolated from solid tissues, tissue sections, and cell lysates. Particularly, the term of "sample" includes the one been treated after collection, for example treating and dissolving with reagents to make them be rich in components like polynucleotides or peptides, and fractions of samples from patients. Samples collected from patients can be used for diagnosis or monitoring. Further, the sample can be collected from mankind or other mammals.

As used herein, the term "octasaccharide" means four disaccharide units composed of eight saccharides.

As used herein, the terms "magnetic beads" and "beads" can be used interchangeably.

Example 1

Design and Fabrication of Microfluidic Chip

Figure 1A:
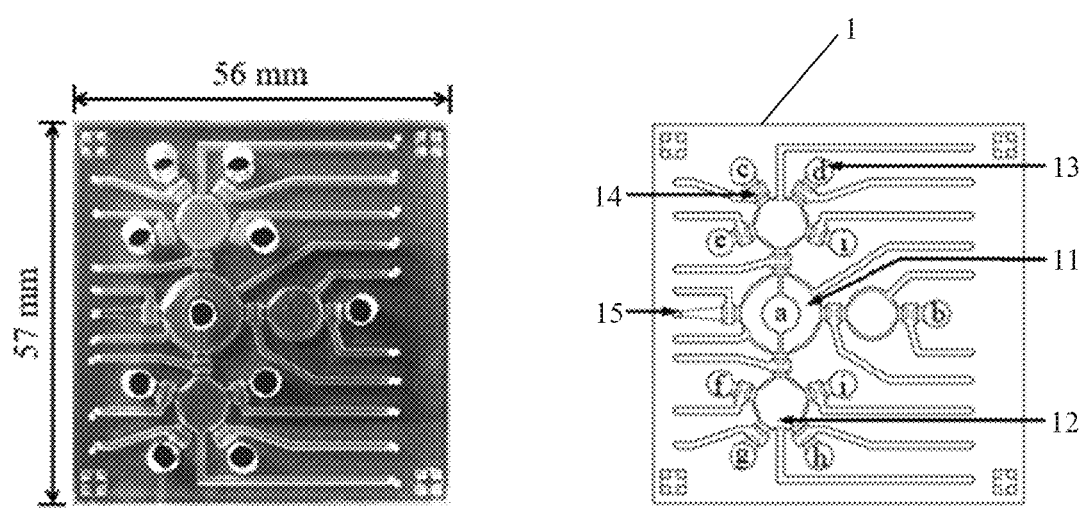
FIG. 1A is a schematic diagram of a microfluidic chip.

The microfluidic platform designed in this example includes a blood cell depletion module, a cancer cell isolation module and an IF staining module. The components on the microfluidic chip 1 are an open-type micromixer 11, a plurality of micropumps 12, eight reagent chambers 13 (including the symbols c, d, e, i, f, g, and h in FIG. 1A), a supernatant reservoir b, a plurality of normally-closed valves 14 and a waste outlet 15, shown in FIG. 1A, wherein a indicates blood sample, b indicates supernatant reservoir, c indicates octasaccharide-coated beads, d indicates CD45-coated beads, e indicates 4% paraformaldehyde, f indicates 0.1% Triton X-100, g indicates primary antibodies, h indicates secondary antibodies (Hoechst 33258), and i indicates wash buffer. The open-type micromixer 11, micropumps 12 and normally-closed valves 14 would be controlled by deforming membranes via applying positive and negative gauge pressures using programs and electromagnetic valves with a home-made machine to perform the mixing and transportation of samples and reagents. By integrating the components mentioned above, the microfluidic chip developed in this example could execute the processes of blood sample pretreatment, cancer cell isolation and IF staining.

Figure 1B:
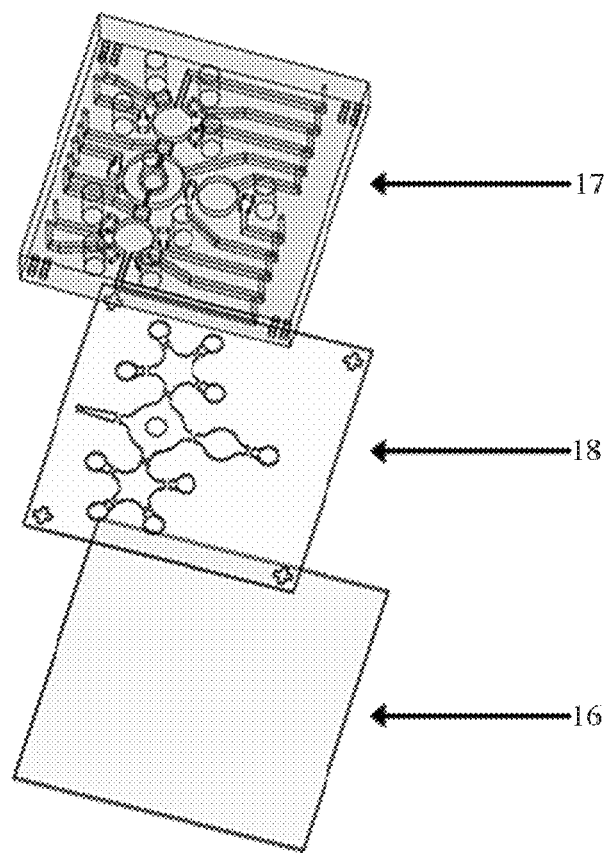
FIG. 1B is a schematic diagram of the assembly of the microfluidic chip.
Figure 1C:
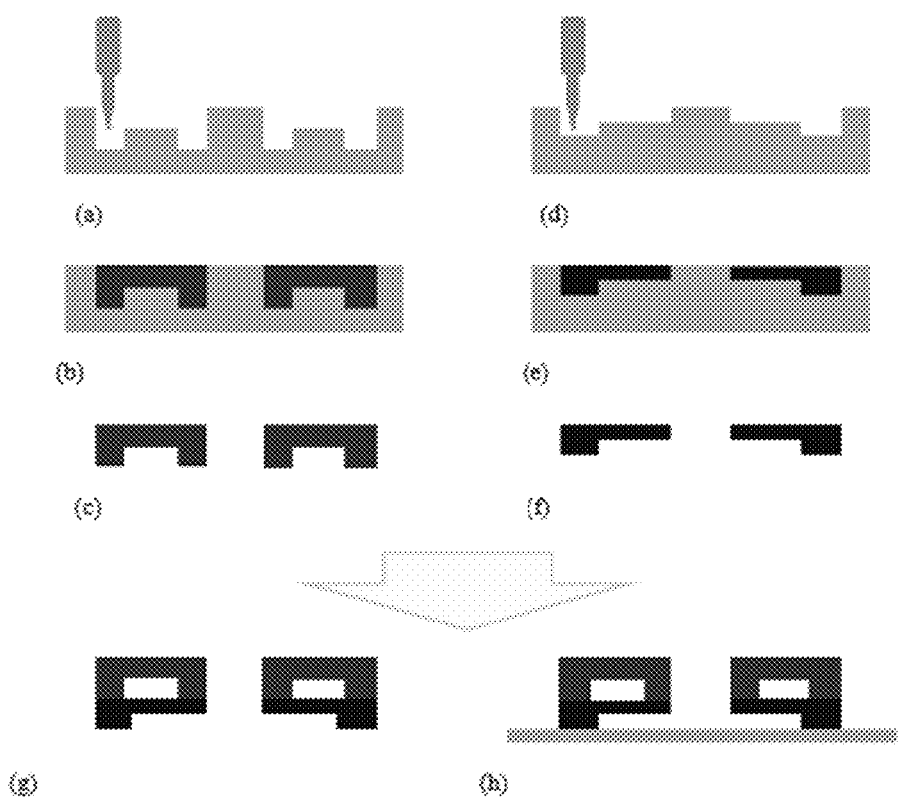
FIG. 1C is a schematic diagram of the fabrication of the microfluidic chip.

The integrated microfluidic chip was fabricated with two polydimethylsiloxane (PDMS) layers and a glass substrate 16 (FIG. 11B). The thick-film PDMS was used as the air channel layer 17, and another thin-film PDMS served as the liquid channel layer 18. The master molds of the air channel layer 17 and liquid channel layer 18 were engraved by the computer-numerical-control (CNC) machine (EGX-400, Roland Inc., Japan) equipped with a 0.5-mm drill. The microstructure of the master mold on polymethylmethacrylate (PMMA) was formed by a process of CNC machining, shown as FIG. 1 C (a) and (d). Then PDMS casting and replica-molding processes were performed to obtain the inverse structures of master molds. PDMS was prepared by mixing the curing agent and the PDMS pre-polymer (Sylgard 184A/B, Sil-More Industrial Ltd., USA) in a ratio of 1:10 by weight, all bubbles were removed by placing it into a vacuum chamber for 40 mins. After removing the bubbles, the master molds were manually filled up with the PDMS mixture and cured at 85° C. for 3 hours (FIG. 1C (b) and (e)). Then the two PDMS layers were peeled off from the master molds which has been illustrated in FIG. 1C (c) and (f), followed by bonding the thick and thin PDMS layers together by the process of plasma oxidation (FIG. 1C (g)). The combined PDMS was finally bonded with the glass substrate by the same procedure of plasma oxidation, shown in FIG. 1C (h).

Example 2

Operating Process on Automatic Microfluidic System

Figure 2:
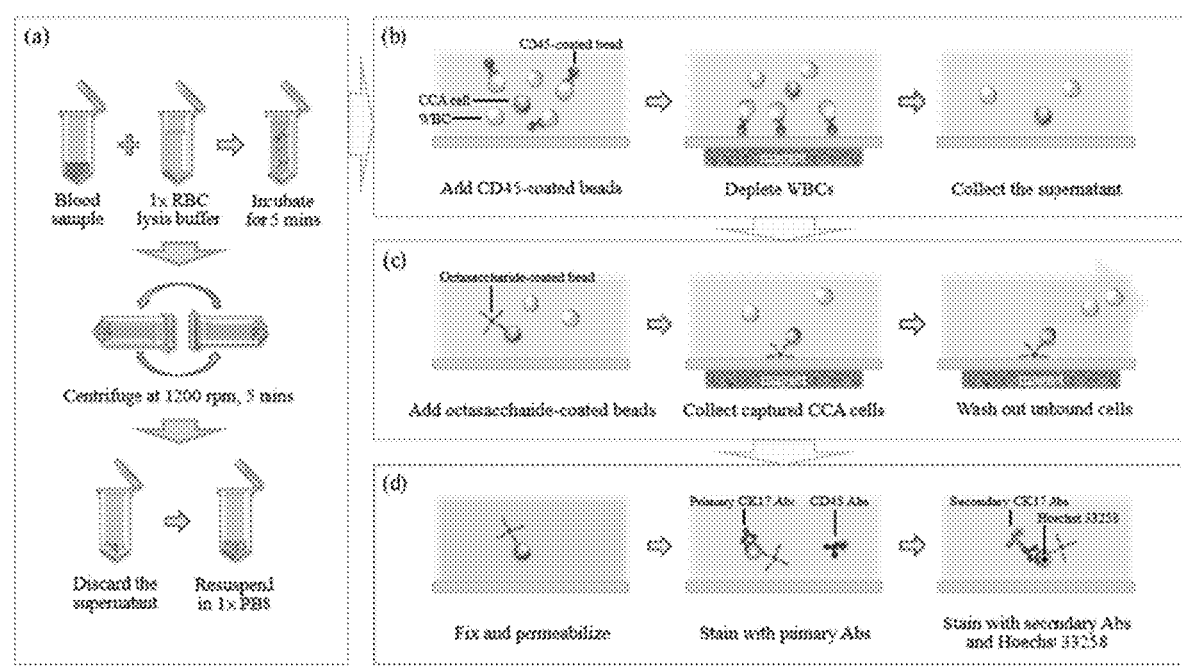
FIG. 2 is a schematic diagram of the operating process of an automatic microfluidic system.
Figure 3A:
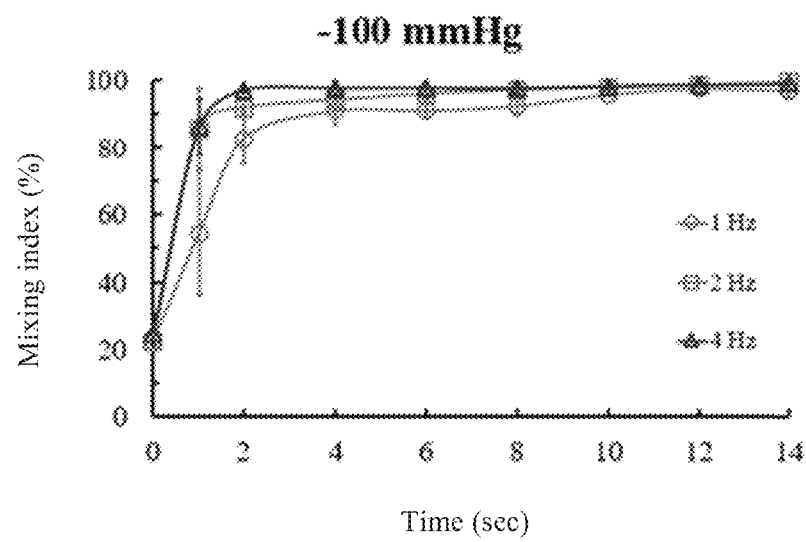
FIGS. 3A to 3E show the mixing index under a gauge pressure of −100 to −500 mmHg.
Figure 3B:
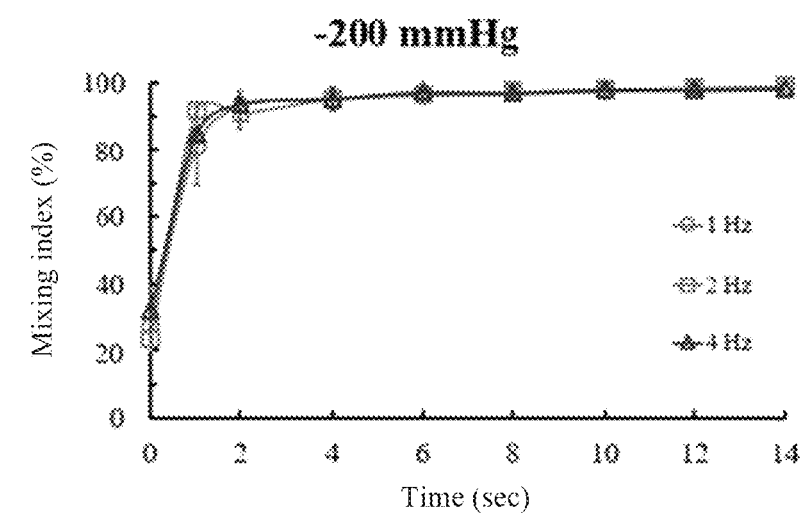
Figure 3C:
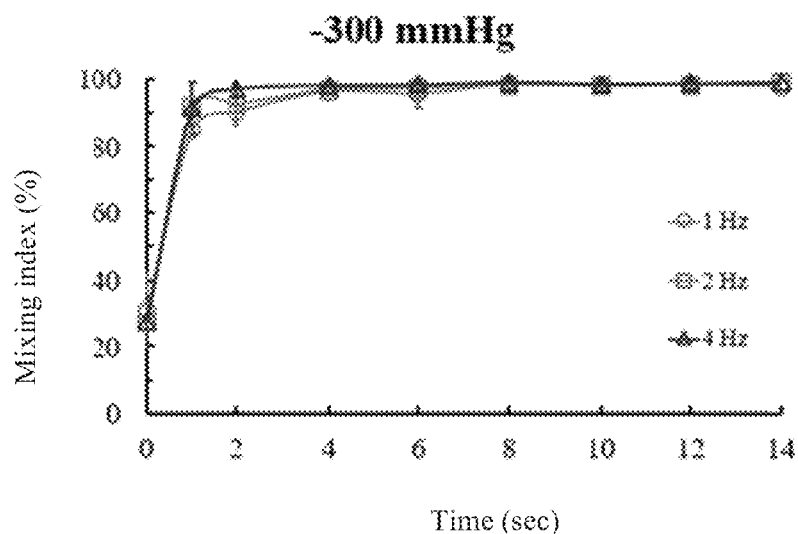
Figure 3D:
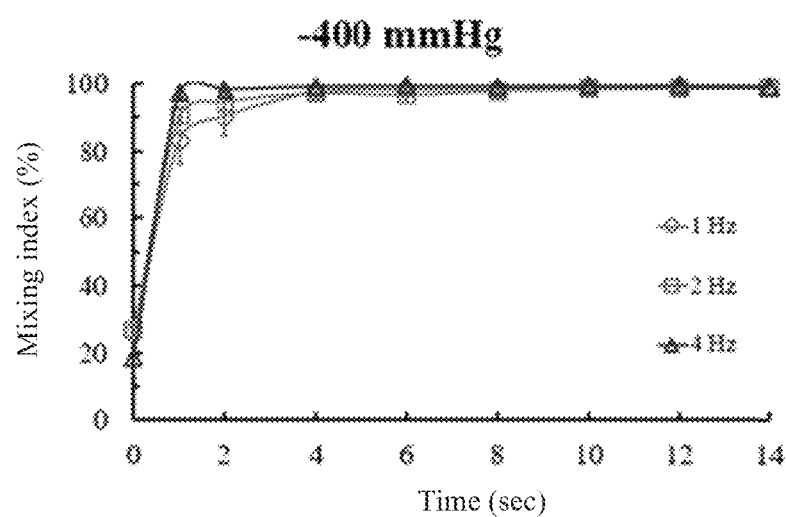
Figure 3E:
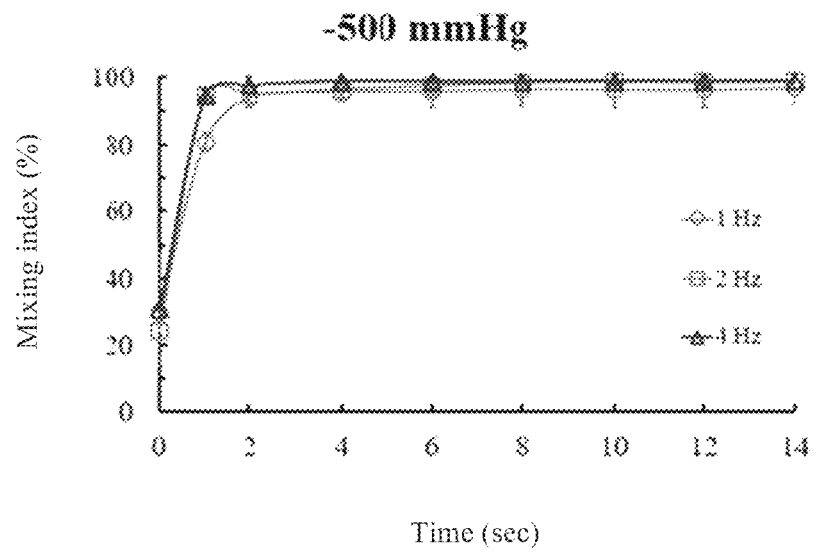

This example reported an integrated microfluidic system which could automatically perform WBC depletion, CCA cell isolation and IF staining. A whole blood sample (2-3 mL) spiked with $10^5$ human cholangiocarcinoma cell line Huh28 cells (supplied by Division of Surgery, National Cheng Kung University Hospital, Taiwan) was pretreated by RBC lysis buffer for 5 mins first. After centrifuging at 1200 rpm for 5 mins and resuspending in 1×PBS (FIG. 2 (a)), the sample was loaded into the micromixer on microfluidic system to execute WBC depletion by Dynabeads® CD45 three times, wherein the Dynabeads® CD45 are CD45-coated beads. In brief, WBCs in the sample were incubated with Dynabeads® CD45 and the captured WBCs were collected by applying a magnet, the supernatant was transferred to the supernatant reservoir followed by washing out the gathered Dynabeads® CD45 and transferring the supernatant back to the micromixer (FIG. 2 (b)). After performing the WBC depletion three times, octasaccharide-coated beads were transferred to the chamber containing CCA cells and were isolated by octasaccharide-coated beads (FIG. 2 (c)) followed by fixation in 4% PFA and permeabilization with 0.1% triton X-100. They were then stained with Hoechst 33258 (nucleic staining dye), positive (CK17) and negative (CD45) Abs, as shown in FIG. 2 (d).

Example 3

Performance of the Microfluidic System

In this example, the microfluidic chip for CCA cell detection consisted of several components such as micromixers, micropumps and microvalves. Before the entire on-chip experiments, the performances of the microfluidic chip including mixing index and shear force was measured, such that the optimum operating conditions could be applied on the microfluidic system.

3.1 Mixing Index of the Micromixer

In order to effectively incubate cells and octasaccharide-coated beads by the pneumatic micromixer, mixing index which could reflect the mixing efficiency of the micromixer was tested and calculated. The two liquid samples chosen for tests of mixing efficiency were 120 µL DI water and 5 µL blue ink. Gauge pressures from −100 to −500 mmHg were applied at driving frequencies of 1, 2 and 4 Hz to cause different mixing efficiencies. The entire operating process of the microfluidic chip was carried out at a constant gauge pressure of 51.7 mmHg on the normally-closed valves. The experiments were performed under a microscopy connected to a cooled charge-coupled-device (CCD) camera (Evolution™ VF Color Cooled, Canada) used to obtain optical images. The captured images were then processed through the digital image processing and analysed with ImageJ to calculate the mixing index. Mixing index (a) is a quantitative performance of mixing efficiency of the micromixer, and given by equation (1):

$$\sigma(A) = \left(1 - \frac{\int_A |C^+ - C_\infty^+| dA}{\int_A |C_0^+ - C_\infty^+| dA}\right) \times 100\% \quad (1)$$

where $C^+$ is the local normalized concentration distributed within the cross-sectional area of mixing chamber (A), and $C_0^-$ and $C_\infty^-$ are concentrations associated with the completely unmixed and completely mixed states, respectively. σ is set to be 0% while the mixture is completely unmixed. On the contrary, σ is 100% if the mixture is fully mixed.

FIGS. 3A to 3E illustrate the mixing indices applied with the gauge pressure from −100 to −500 mmHg, and each of them was performed at the three chosen frequencies (1 Hz, 2 Hz and 4 Hz). The results of the five applied gauge pressure depict that the best mixing performance was at 4 Hz. Complete mixing was achieved within 2 secs when being applied with −100, −200 and −300 mmHg at 4 Hz, and only 1 sec was needed to mix by applying a pressure of −400 or −500 mmHg at the same driving frequency. Mixing indices of the five gauge pressures applied at 4 Hz reached about 97%. From the results of mixing index test, the gauge pressure, −400 mmHg, applied at 4 Hz would be the optimum operational condition for incubation on the microfluidic chip. However, it still required reference to the results of shear force test for the micromixer to optimize the optimum operating condition for incubating cells and octasaccharide-coated beads. The results of shear force test have been illustrated as follows.

3.2 Shear Force of the Micromixer

For the purpose of avoiding any binding disruption between the receptor on the cell surface and octasaccharide, this example would like to realize the gentle mixing within the pneumatic micromixer by controlling the shear force. In this example, polystyrene beads (Ø=40 µm, 4240A, Thermo Fisher Scientific, USA) suspended in the DI water were selected for testing and calculating the shear force. Applied gauge pressures were the same as chosen for measurements of mixing index, that is from −100 to −500 mmHg and at a driving frequency of 0.5 Hz to form different flow velocities of the plastic beads, and at a constant gauge pressure of 51.7 mmHg supplied to the normally-closed valves. The experiments were performed under a microscopy connected to a cooled charge-coupled-device (CCD) camera (Evolution™ VF Color Cooled, Canada). Camera lens was set to the mid-height of the chamber and flow velocity of plastic beads was measured by digital image processing and analysis of captured images to calculate the shear force, given by equation (2):

$$\text{Shear force} \sim \tau A = \frac{\mu du}{dy} A \sim \frac{\mu \Delta u}{\Delta y} A \qquad (2)$$

where $\tau$ is shear stress, $\mu$ is dynamic viscosity ($H_2O$, 25° C.=$0.89 \times 10^{-3}$ Ns/m$^2$), u is the flow velocity of plastic bead, y is the mid-height of the chamber (y=$3 \times 10^{-4}$ m), and A is the area of annular filed (A=$3.28 \times 10^{-6}$ m$^2$).

Figure 4:
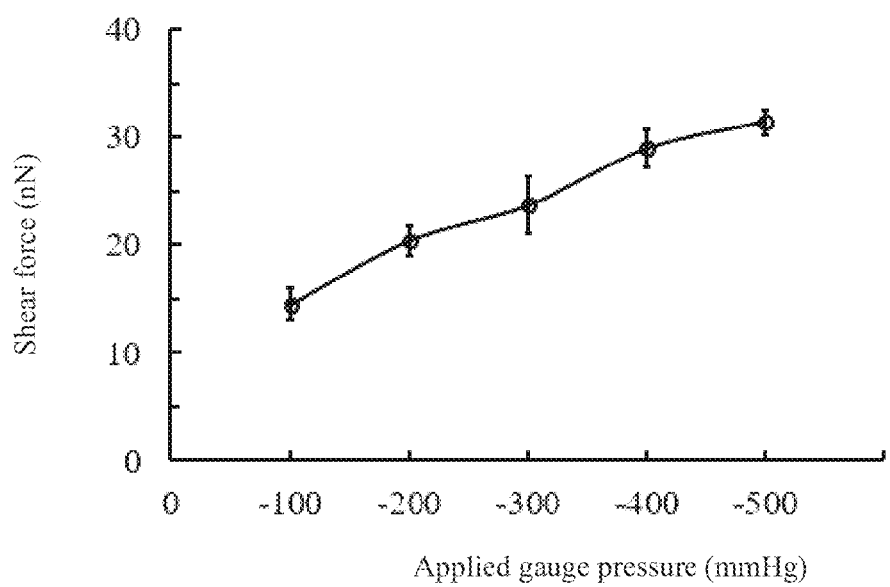
FIG. 4 is a data diagram of the shear force of the micromixer.

It could be observed that higher the gauge pressure applied, higher the shear force as shown in FIG. 4. The measured wall shear forces under each applied gauge pressure were 15±2 nN, 20±1 nN, 24±3 nN, 29±2 nN and 31±1 nN, respectively. In order to achieve the capture of cells by octasaccharide via gentle mixing, the selection of optimum gauge pressure was integrated with the results of mixing index test. Although, −400 mmHg was the best operating condition for complete mixing, −100 mmHg pressure would be optimum for gentle mixing such that there is sufficient binding between cells and octasaccharides in only 2 secs. Therefore, applied gauge pressure of −100 mmHg at a driving frequency of 4 Hz was chosen as the optimum operating condition for the micromixer integrated on the microfluidic system.

Example 4

The Specificity Test of Octasaccharides Using Capture Efficiency

The cell lines utilized in this example were SNU478, HuCCT1, Huh28, KKU100, MMNK1, BxPC3, HepG2 and HCT8, SNU478, HuCCT1, Huh28, KKU100, and MMNK1 were supplied by Division of Surgery, National Cheng Kung University Hospital, Taiwan. BxPC3 and HepG2 were supplied by Dr. Kuang Hung Cheng, Institute of Biomedical Science, National Sun Yat-sen University, Taiwan. HCT8 was supplied by Professor Hwan-You Chang, Institute of Life Science, National Tsing Hua University, Taiwan. SNU478, HuCCT1, Huh28 and KKU100 were used as target cells for positive selection, which are CCA cell lines respectively derived from the ampulla of Vater, the intrahepatic-metastasized ascites, the intrahepatic bile duct and the opisthorchis viverrini-related hilar bile duct. For negative selection, MMNK1 (immortalized biliary epithelial), and various types of cancer cell lines, including BxPC3 (pancreatic cancer), HepG2 (liver cancer) and HCT8 (colorectal cancer) were used. Among these cell lines, SNU478, HuCCT1, Huh28, BxPC3 and HCT8 were identically cultured in Roswell Park Memorial Institute 1640 (RPMI 1640, Gibco®, Thermo Fisher Scientific, USA) containing 100 U/mL penicillin and 100 μg/mL streptomycin (Pen Strep, Gibco®, Thermo Fisher Scientific, USA), 10% fetal bovine serum (FBS, Gibco®, Thermo Fisher Scientific, USA). The growth medium for KKU100, MMNK-1 and HepG2 was Dulbecco's modified eagle medium (DMEM, Gibco®, Thermo Fisher Scientific, USA) complemented with the additives described above. All cells were cultured in a humidified incubator at 37° C. under an atmosphere containing 5% $CO_2$.

In this example, the cells were captured by magnetic beads. The surface of magnetic beads was coated, respectively, with three concentrations of ten kinds of heparan sulfate (HS) octasaccharides, that is, from SCH-43 to SCH-52. The magnetic beads used in this example were Dynabeads® MyOne™ Streptavidin T1 (~7-10×10$^9$ beads/mL, Ø=1 μm, Invitrogen, Thermo Fisher Scientific, USA). Briefly, each octasaccharide of 1 μM, 10 μM and 100 μM concentration were first incubated with magnetic beads in a volume/volume ratio of 1:10, and placed on the wheeling rotator (RM-2L INTELLI-mixer, ELMI Ltd., Latvia) at 25 rpm, C2 mode for 30 mins at room temperature. The beads were then collected using a magnetic particle concentrator (MPC, Dynabeads® MPC®-1, Life Technologies) for 2 mins, followed by discarding the supernatant and washing the coated beads three times with 1 mL of deionized (DI) water. Finally, the coated beads were suspended in the same volume of DI water as the initial volume of Dynabeads®.

Figure 5A:
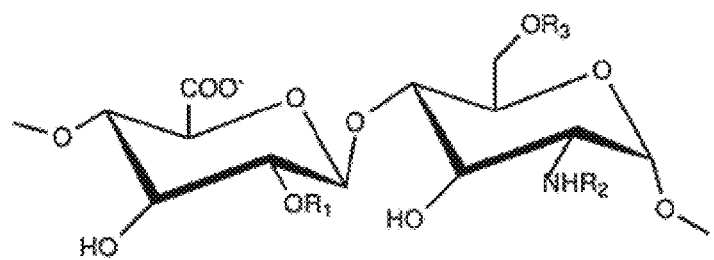
FIG. 5A is a schematic diagram showing the structure of a disaccharide unit of an octasaccharide.
Figure 5B:
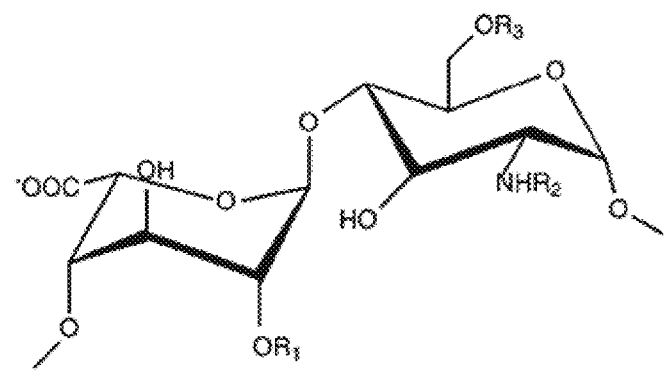
FIG. 5B is a schematic diagram showing the other structure of the disaccharide unit of the octasaccharide.

The ten kinds of octasaccharides used to identify the cells were synthesized by Dr. Shang-Cheng Hung affiliated to Genomics Research Center at Academia *Sinica*, Taiwan. The structures of these ten octasaccharides were composed of four variably sulfated disaccharide units consisting a N-acetyl-α-D-glucosamine (α-D-GlcNAc), and a β-D-glucuronic acid (β-D-GlcA) (FIG. 5A) or α-L-iduronic acid (α-L-IdoA) (FIG. 5B) jointed by 1→4 linkage followed by a biotin for the purpose of binding with the streptavidin on Dynabeads®. It was through a series of enzymatic procedures to modify this backbone described above, including sulfonation at the N and/or O6 positions of α-D-GlcNAc (shown as NS and 6S), and at the O2 positions of β-D-GlcA/α-L-IdoA (shown as 2S). The symbols of α-D-GlcNAc, β-D-GlcA and α-L-IdoA were respectively defined as ■, ◇ and ◆. By the combination of repeating disaccharide units, the ten octasaccharides from SCH-43 to SCH-52 were classified into two groups which were (NININININI) and

(NINGNING). SCH-43 and SCH-49~52 were members in the NINININI group, and the backbones of SCH-44~48 were the NINGNING group. The differences of sulfonated position between SCH-43~52 has been shown as follows.

The biologic depiction of the octasaccharide SCH-43 is

, and the octasaccharide SCH-43 has the following structural formula:

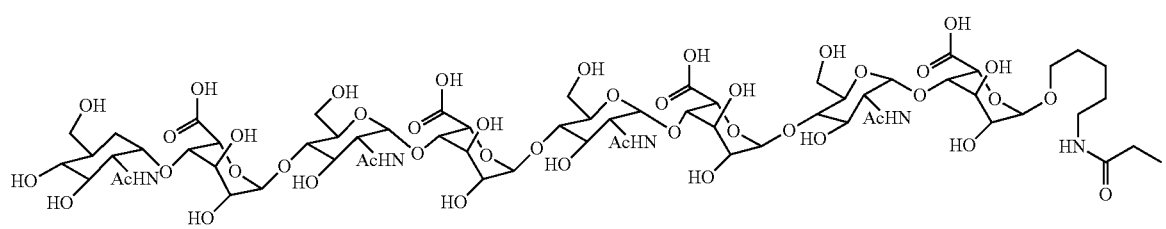

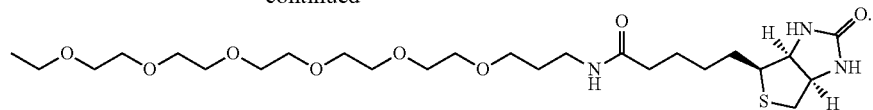
The biologic depiction of the octasaccharide SCH-49 is
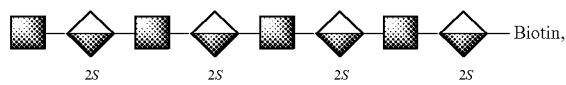
and the octasaccharide SCH-49 has the following structural formula:
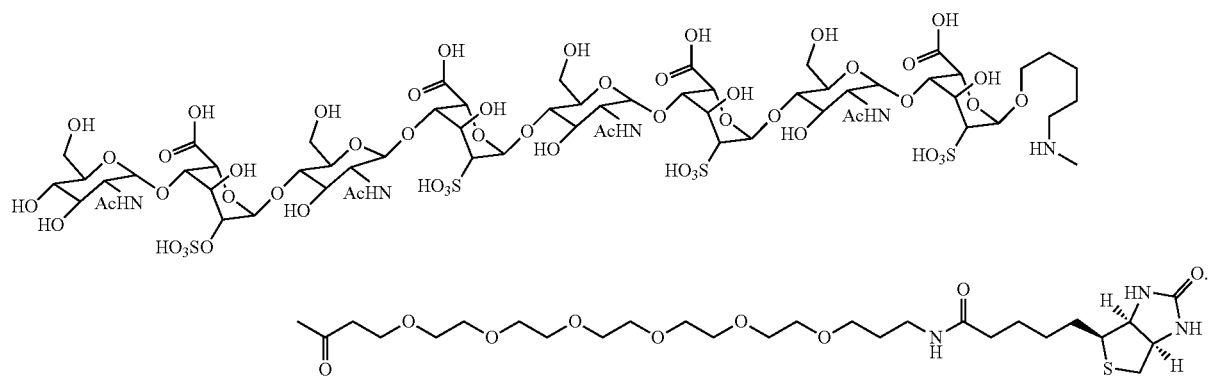
The biologic depiction of the octasaccharide SCH-50 is
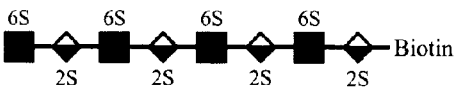
, and the octasaccharide SCH-50 has the following structural formula:
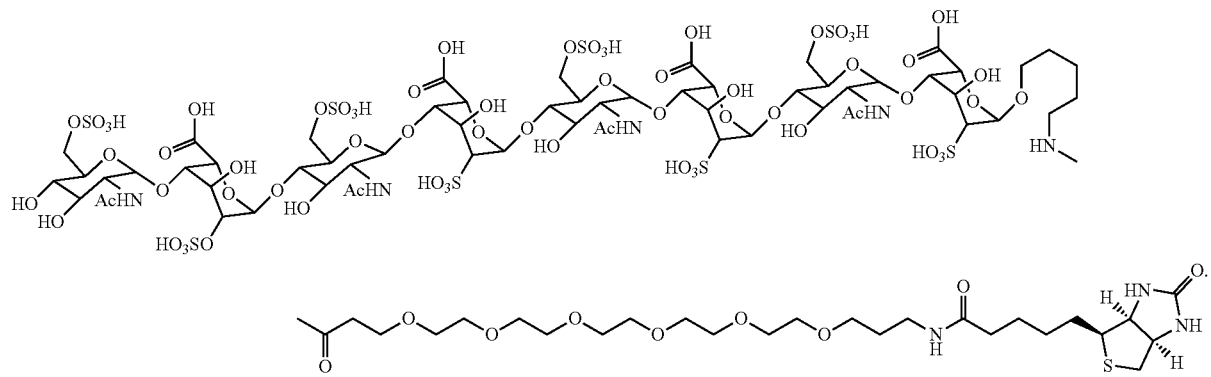
The biologic depiction of the octasaccharide SCH-51 is
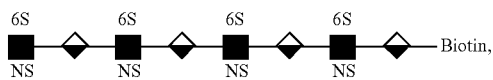
and the octasaccharide SCH-51 has the following structural formula:

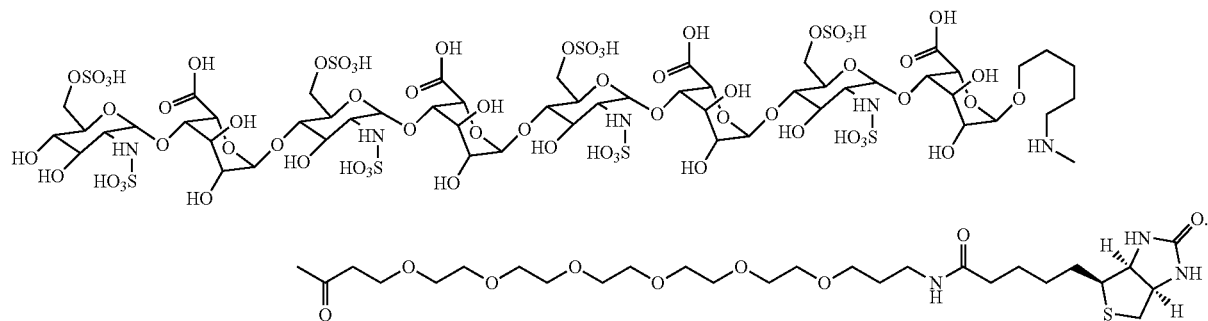
The biologic depiction of the octasaccharide SCH-52 is
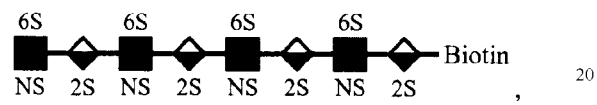
and the octasaccharide SCH-52 has the following structural formula:
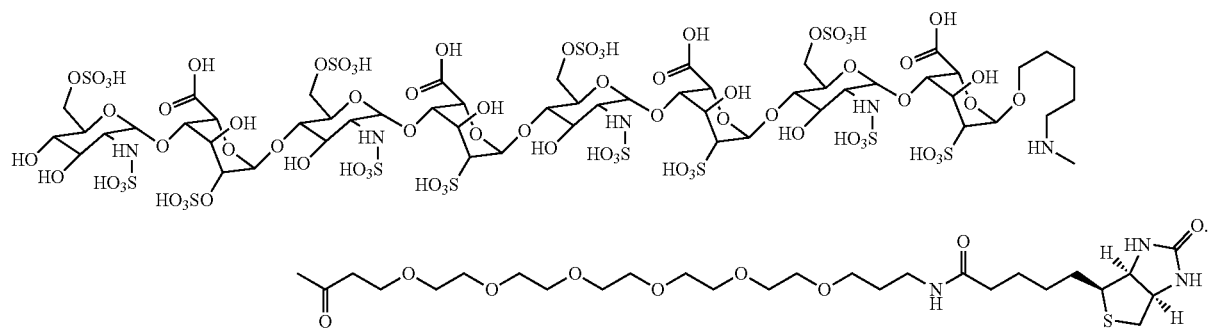
The biologic depiction of the octasaccharide SCH-44 is
and the octasaccharide SCH-44 has the following structural formula:
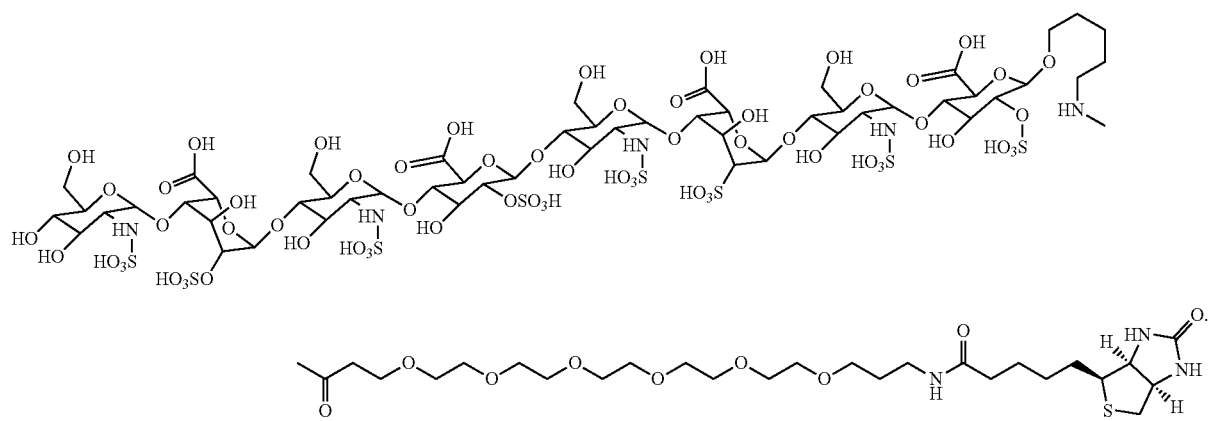

The biologic depiction of the octasaccharide SCH-45 is

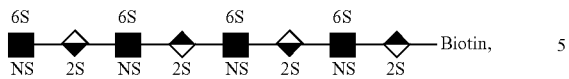

and the octasaccharide SCH-45 has the following structural formula (I):

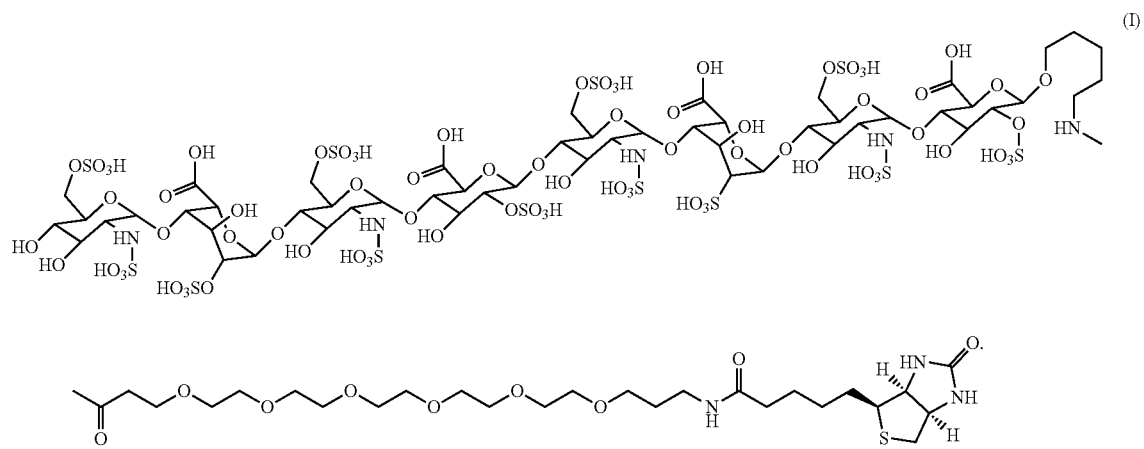

The biologic depiction of the octasaccharide SCH-46 is

and the octasaccharide SCH-46 has the following structural formula (II):

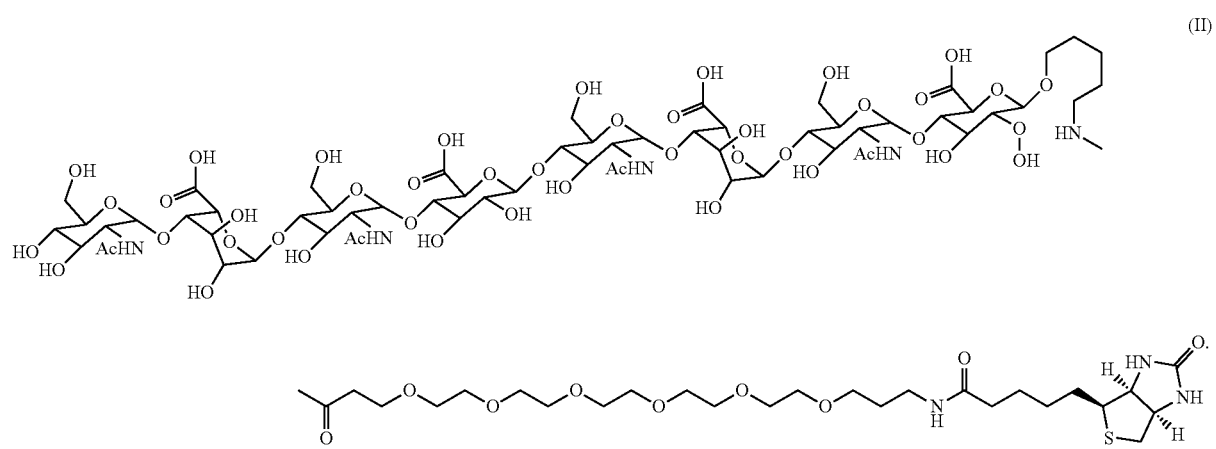

The biologic depiction of the octasaccharide SCH-47 is

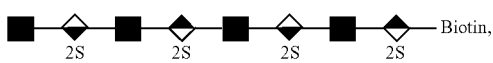

and the octasaccharide SCH-47 has the following structural formula:

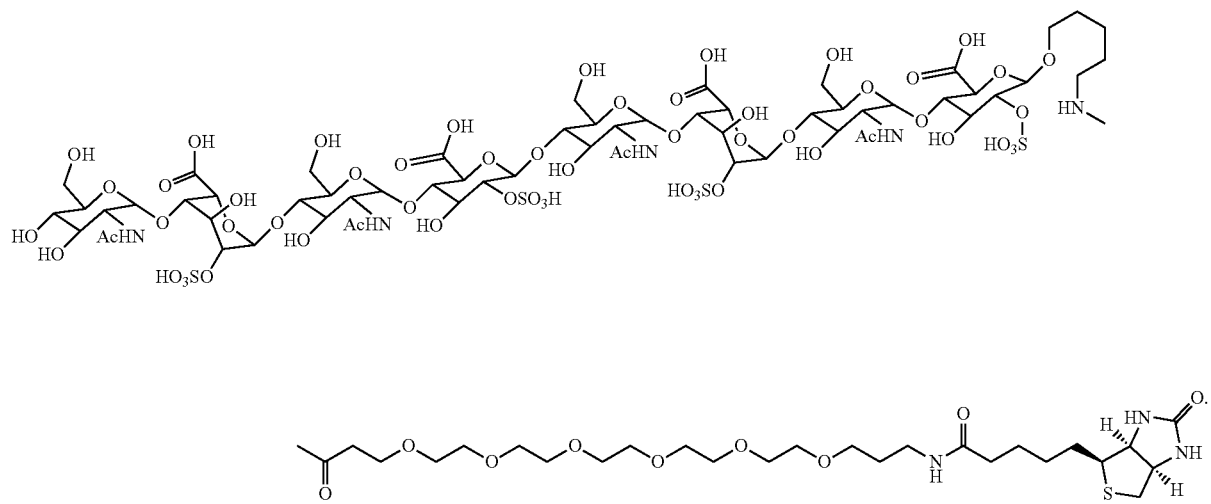

The biologic depiction of the octasaccharide SCH-48 is

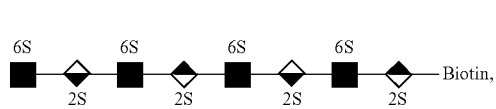

and the octasaccharide SCH-48 has the following structural formula:

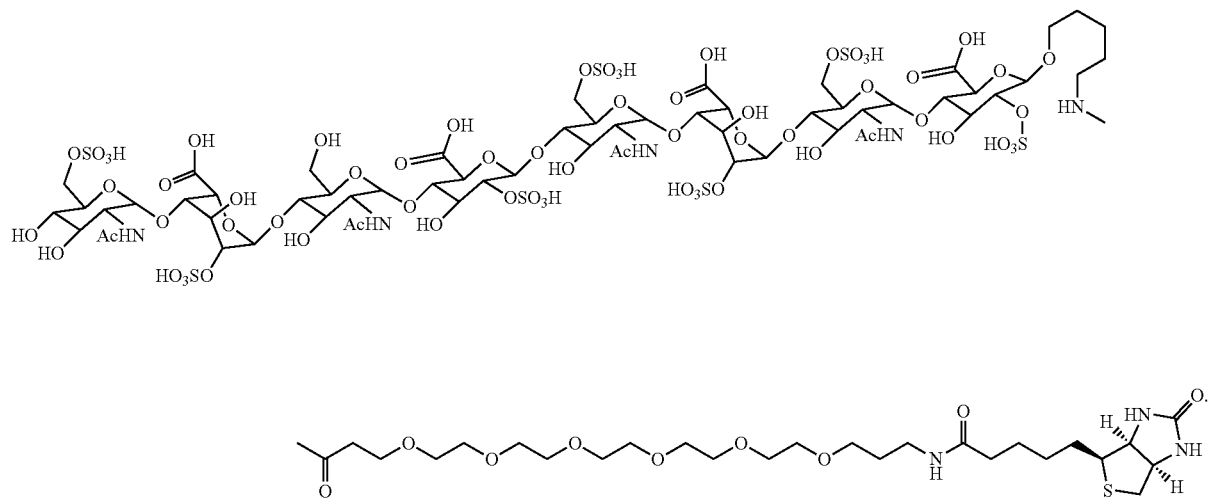

In this example, the capture test for the eight cell lines mentioned above was performed with ten octasaccharides to determine their affinity. Therefore, by using the traditional shaker, $2\times10^5$ cells were incubated with three kinds of concentration (1 µM, 10 µM and 100 µM) of each octasaccharide for 30 mins. After the incubation, they were washed twice and the amount of captured cells was calculated by a hemocytometer under an inverted microscope. Through statistical analysis by ANOVA, the octasaccharides which bound to one cell line with high specificity was compared to other cell lines. Table 1 shows the capture rate of various cell lines bound by the beads pre-coated with octasaccharides SCH-45 and SCH-46.

TABLE 1

| Octa-saccharide Concentration | SCH-45 (%) | | | SCH-46 (%) | | | EpCAM |
|---|---|---|---|---|---|---|---|
| (µM) | 1 | 10 | 100 | 1 | 10 | 100 | (%) |
| MMNK1 | 55 ± 7 | 47 ± 20 | 16 ± 8 | 58 ± 11 | 52 ± 6 | 34 ± 5 | 58 ± 80 |
| SNU478 | 20 ± 5 | 17 ± 7 | 16 ± 8 | 23 ± 13 | 20 ± 8 | 22 ± 7 | 74 ± 60 |
| HuCCT1 | 5 ± 1 | 5 ± 2 | 4 ± 2 | 4 ± 1 | 6 ± 2 | 4 ± 1 | 67 ± 11 |
| Huh28 | 66 ± 6 | 67 ± 3 | 73 ± 4 | 65 ± 20 | 70 ± 10 | 78 ± 14 | 58 ± 19 |
| KKU100 | 42 ± 3 | 44 ± 2 | 41 ± 11 | 40 ± 10 | 46 ± 1 | 51 ± 2 | 51 ± 50 |

TABLE 1-continued

| Octa-saccharide Concentration ($\mu M$) | SCH-45 (%) | | | SCH-46 (%) | | | EpCAM (%) |
|---|---|---|---|---|---|---|---|
| | 1 | 10 | 100 | 1 | 10 | 100 | |
| HepG2 | 14 ± 1 | 11 ± 4 | 9 ± 6 | 12 ± 0 | 16 ± 6 | 10 ± 4 | 44 ± 70 |
| BxPC3 | 16 ± 6 | 11 ± 3 | 7 ± 3 | 15 ± 5 | 18 ± 4 | 13 ± 7 | 45 ± 60 |
| HCT8 | 16 ± 3 | 13 ± 0 | 9 ± 2 | 18 ± 5 | 14 ± 4 | 13 ± 3 | 22 ± 3 |

As shown in Table 1, among the ten octasaccharides used in this example, SCH-45 and SCH-46 were highly specific to Huh28, a CCA cell line. The highest capture rate of Huh28 captured by SCH-45 and SCH-46 of 100 μM-coated beads were respectively 73±4% and 78±14%. They were significantly higher than other kinds of cell lines, even bile normal cell line, MMNK-1, whose capture rates were 16±8% and 34±5%, respectively. SCH-45 and SCH-46 were capable of capturing more than 70% of Huh28 which was higher than that captured by EpCAM-coated beads whose capture rate was only 58±19%. Furthermore, EpCAM was unable to distinguish MMNK1 and other kinds of cells, leading to false diagnosis.

Example 5

Test of Octasaccharides as Promising Tools for Use in Clinical Examination at an Early Stage or on the Prognostic Tracking of Cancer In order to determine whether SCH-45 and SCH-46 can be promising tools for use in clinical examination at an early stage or on the prognostic tracking of cancer, such as blood test, an on-bench capture test of WBCs using SCH-45 and SCH-46 of 100 μM-coated beads was performed in this example.

The whole blood used in this example was provided by National Cheng Kung University Hospital and stored at 4° C. (IRB number: A-ER-103-063 and A-ER-105-109). In order to achieve good efficiency in cancer cell capturing using octasaccharide-coated beads with the blood sample, whole blood was pretreated to remove blood cells, including red blood cells (RBCs) and white blood cells (WBCs). In other words, the whole blood pretreatment process contained a RBC lysis step and a WBC depletion step. Since the microfluidic system developed in the invention was found to efficiently detect Huh28 cells by SCH-45 or SCH-46-coated beads, Huh28 cells were spiked in whole blood in order to simulate CTCs detection with CCA patient's blood sample. Whole blood was inoculated with $10^5$ Huh28 cells in a 1.5 mL Eppendorf tube. Then, on-bench RBC lysis was performed using a commercial RBC lysis buffer (Cat. 420301, BioLegend®, USA) diluted to 1× working concentration with DI water. The 100 μL of spiked sample was incubated with 1×RBC lysis buffer at a 1:10 volume/volume ratio on a wheeling rotor at 25 rpm, C2 mode for 5 mins, and then centrifuged at 1200 rpm for 5 mins to discard the supernatant. The pellets were washed twice and resuspended in 100 μL of 1× phosphate buffered saline (PBS) buffer.

Following the RBC lysis step, a WBC depletion step was performed. WBCs would be captured by Dynabeads® CD45 ($4\times10^8$ beads/mL, Ø=4.5 μm, Invitrogen, Thermo Fisher Scientific, USA), when mixed with the above in a 7:1 ratio. That is $7\times10^7$ beads for 1 mL whole blood, and it was indicated that three-time depletion could remove 99.8% WBCs to decrease the interference of capture efficiency for the target cell. After RBC lysis, 100 μL of resuspended solution including approximately $10^5$ to $10^6$ WBCs was then mixed with $7\times10^6$ Dynabeads® CD45 by the wheeling rotator at 25 rpm, C2 mode for 30 mins at room temperature. After separation of bead-WBC complexes using a magnetic particle concentrator for 2 mins, the supernatant was transferred to a new microcentrifuge tube. On-bench WBC depletion process was repeated two times to remove most of the WBCs, followed by an incubation period of 30-min for CCA cells to be captured on bench by SCH-45-coated beads or SCH-46-coated beads.

2 mL whole blood was pretreated by RBC lysis buffer, and divided into two equal volumes to execute the capture tests of WBC with and without WBC depletion. The one with WBC depletion was performed three times by incubation with Dynabeads® CD45 for 30 mins, magnetic separation and washing out WBCs captured by beads. Then, mixing with octasaccharide-coated beads for 30 mins to calculate the number of captured WBCs. The result is shown in Table 2.

TABLE 2

| Octasaccharide Concentration ($\mu M$) | SCH-45 (cells) 100 | SCH-46 (cells) 100 |
|---|---|---|
| Without depletion | 60000 | 30000 |
| Depletion three times | 40 | 13 |

Table 2 indicated the numbers of captured WBCs by SCH-45 and SCH-46 of 100 μM-coated beads via depletions or not. It could be observed that, without depletion, the numbers of captured WBCs using SCH-45 and SCH-46-coated beads were respectively about $6\times10^4$ and $3\times10^4$ cells. For clinical samples, the huge numbers of WBCs would influence the capture efficiency of few CTCs by octasaccharide-coated beads resulting in false diagnosis. However, the amounts of captured WBCs were significantly reduced to less than 50 cells when WBC depletion was performed thrice, such that the influence of WBC on the capture of CTCs would be cut down in turn improving the diagnostic accuracy. According to affinity and specificity tests for cell lines and WBCs by octasaccharides, ratios of WBC capture rate to CCA were $5\times10^{-5}$ and $1\times10^{-5}$ tested by SCH-45 and SCH-46 respectively. Results indicated that SCH-45 and SCH-46 specifically recognized Huh28 with high capture rate but not WBCs. Therefore, SCH-45 and SCH-46 can be promising affinity reagents for the diagnosis of CTCs at an early stage or prognosis of cancer with blood samples from CCA patients.

Example 6

Cell Capture by Using the Microfluidic System
6.1 Incubation Time Between Cells and Octasaccharide-Coated Beads The capture test of every cell line described above was realized using the microfluidic system. In order to confirm the affinity of octasaccharides for CCA and other cancer cell lines, the mixing processes between cell lines and octasaccharides were carried out on the integrated microfluidic platform. The number cells caught by the beads coated with octasaccharides was observed and calculated by a hemocytometer under the inverted microscope. And the capture rate (equation (3)) between the cell lines and beads coated with octasaccharides was presented as follows:

$$\text{Capture rate} = \frac{\text{Number of bound cells}}{\text{Number of initially loaded cells}} \times 100\% \quad (3)$$

Figure 6A:
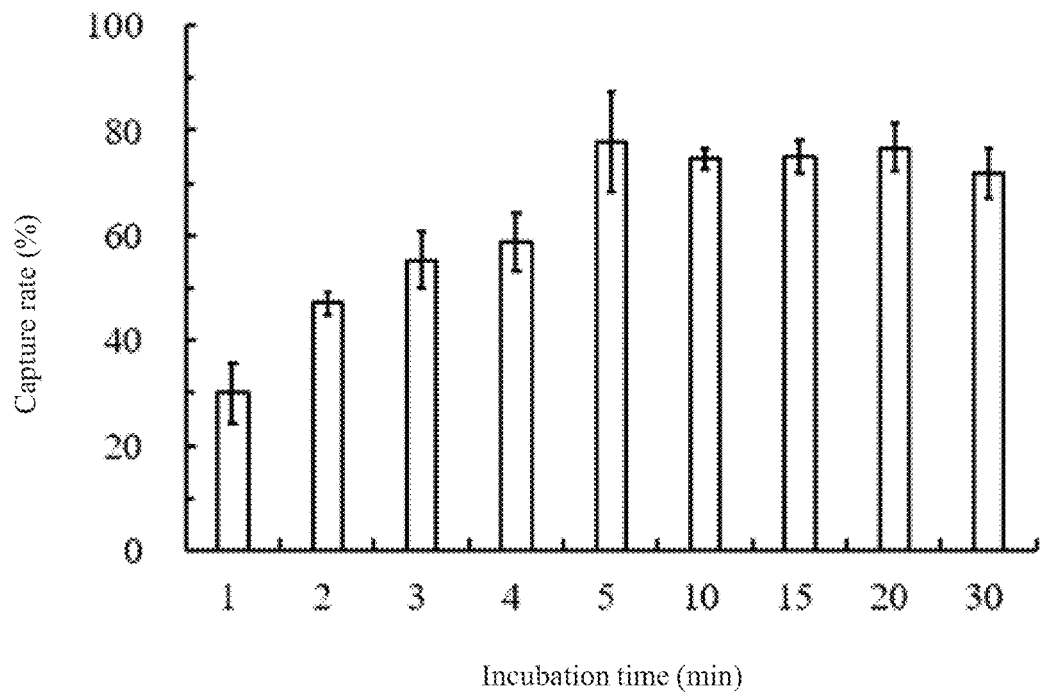
FIG. 6A shows the relationship between the capture rate of Huh28 cells and the reaction time using the octasaccharide SCH-46 (having the structural formula (II)) of 100 µM-coated beads.

For the purpose of obtaining the high affinity between cells and octasaccharides with precise control and prevention of any artificial error, the experiment procedures were moved from bench top to the microfluidic chip designed in the invention. Furthermore, to realize high efficiency of detection process using the microchip, the incubation time between target cells and octasaccharide-coated beads was tested. FIG. 6A shows the relationship between capture rate of Huh28 cells and incubation time using SCH-46 of 100 µM-coated beads. The capture rates were illustrated to increase until mixing for 5 mins, and became saturated after 5-min of incubation. Therefore, the optimum incubation time on chip was set to be 5 mins, the capture rate was 78±9% similar to the one using the traditional shaker. However, the mixing time was greatly shortened compared to nearly 30 mins on bench while achieving similar capturing efficiency for the target cells, Huh28.

6.2 Immunofluorescence Staining for CCA Cells Spiked in Whole Blood

In this example, the procedure for on-chip WBC depletion included injecting the resuspended solution into the micromixer of the developed microchip. Then, Dynabeads® CD45 were transferred from the storage chamber to the micromixer and allowed to incubate at a driving frequency of 4 Hz under −100 mmHg of applied gauge pressure. After mixing for 10-min, a magnet (~2980-3200 Gauss, Ø=10 mm) was used to separate bead-WBC complexes for 2 mins. The supernatant was transported to the supernatant reservoir, and bead-WBC complexes were discarded by applying suction. Entire WBC depletion procedure described above was also repeated two times, followed by 5-min for capture of CCA cells on chip by SCH-46-coated beads.

The spiked sample was pretreated for RBC lysis and WBC depletion in advance, and then Huh28 cells were captured using SCH-46-coated beads followed by IF staining with the positive, negative antibodies (Abs) and nucleic acid stains, namely CK17, CD45 and Hoechst 33258. It indicated that CK17 was highly specific and sensitive to CCA cells, and CD45 could recognize WBCs. After on-chip WBC depletion, there were still about 0.2% WBCs remaining. In order to avoid the misjudgment by non-specific binding of WBC with SCH-46, cells captured by SCH-46-coated beads were stained using the above reagents for confirmation.

Prior to bench-top IF staining with CK17, CD45 and Hoechst 33258, bead-cell complexes were pretreated by 5-min of fixation in 4% paraformaldehyde (PFA, Amresco, LLC., USA) and 5-min permeabilization with 0.1% triton X-100 (Sigma, USA). Then, 1 µL primary CK17 Abs (100 µL, 0.6 µg/mL, GTX103765, Rabbit, GeneTex, USA) and 1 µL CD45 Abs (ARG21370, Arigo Biolaboratories Corporation, Taiwan) was diluted with 50 µL 1×PBS containing 3% bovine serum albumin (BSA, Sigma-Aldrich), and incubated with bead-cell complexes for 60 mins. After washing out unbound primary Abs, 1 µL of fluorescence-labelled secondary CK17 Abs (goat anti-rabbit IgG Alexa 488; GeneTex, USA) were appropriately diluted with 50 µL 1×PBS and mixed with the sample for 30 mins. Then, 1 µL Hoechst 33258 (Invitrogen, USA) was also diluted by 50 µL 1×PBS and used to stain cell nuclei for 5 mins. All steps of IF staining were performed at room temperature.

Compared to the procedure of bench-top IF staining, the sample treated via WBC depletion and CCA cell isolation on the microfluidic system was fixed and permeabilized as described above. After washing twice, diluted primary CK17 Abs and CD45 Abs were transported to the micromixer and incubated with bead-cell complexes for 30 mins. After the magnetic separation of bead-cell complexes and washing out of unbound Abs, the diluted secondary CK17 Abs and Hoechst 33258 were transferred to the micromixer and mixed for 5 mins. Then, unbound secondary Abs and Hoechst were removed. Processed sample was taken out from the micromixer and loaded on the slide to be observed under an inverted microscope with a digital control module. All bright-field and fluorescent images were finally captured by NIS-Elements Basic Research software (Br, version 4.20.00, 64 bit, Nikon, Japan).

Figure 6B:
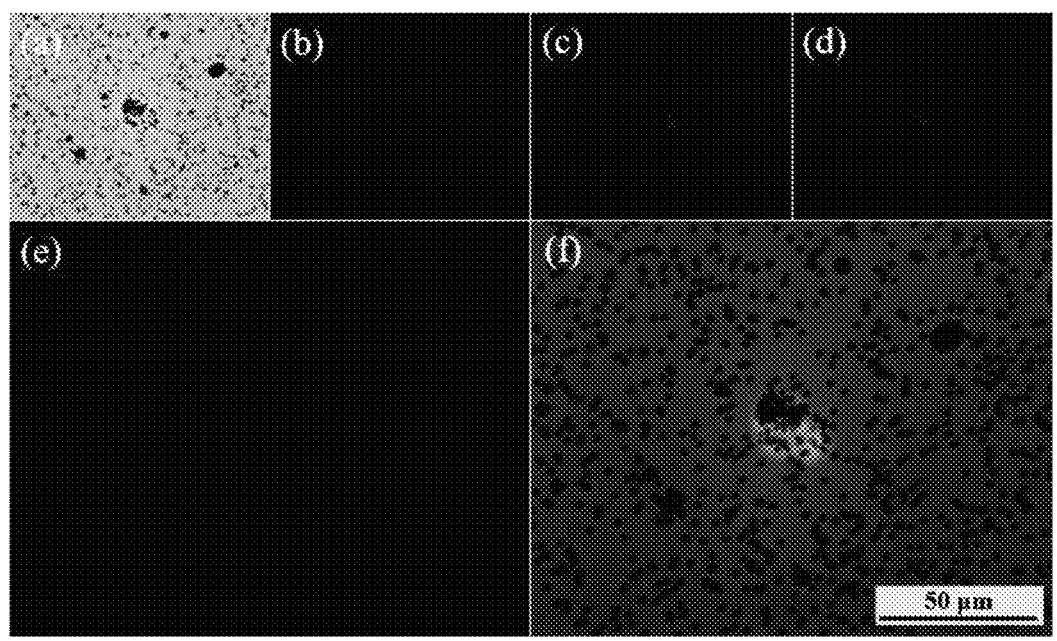
FIG. 6B is a diagram of immunofluorescence staining for cholangiocarcinoma (CCA) cells spiked in whole blood.

The whole detection process for CCA cells spiked in whole blood composed of one off-chip RBC lysis process, one on-chip WBC depletion process, one on-chip CCA cell capturing and one on-chip IF staining process. The captured cells by SCH-46-coated beads were then stained by Hoechst 33258 (blue), CK17 (green, positive) and CD45 (red, negative) for confirmation. FIG. 6B (a) showed the bright-field image of cells captured by SCH-46-coated beads, and fluorescent signals of Hoechst 33258, CK17 and CD45 have been shown in FIG. 6B (b), (c) and (d), respectively. All image were merged and have been shown in FIG. 6B (e). It could be observed that the captured cells were successfully stained by Hoechst 33258 and CK17 without CD45, and the result indicated that the captured cells were CCA cells. Therefore, the developed microfluidic system was capable of realizing the detection procedures of CCA cells spiked in whole blood. Compared to CellSearch® system, SCH-46 was used as a reagent with highly specificity and affinity to isolate CCA cells from other elements in the sample, superior to EpCAM. It is worth nothing that the time taken for the entire detection process was reduced from 4 to 2 hrs by using the microfluidic system.

Example 7

Bench-Top CTC Detection with Clinical Samples

Blood specimens from a normal person and two iCCA patients were pretested by on-bench CTC detection procedure. Each blood sample (3 mL) was processed for RBC lysis, WBC depletion, CCA cell isolation and IF staining steps. Some cells captured by SCH-46-coated beads from the treated patient blood sample were detected and stained by Hoechst. The captured cells were further confirmed by fluorescence signals of CK17 and CD45 Abs. Cells showed CK17 but no CD45 signals which further confirms them as being CCA cells (positive cells). On the contrary, if the cells have CD45 signals, they were defined as non-CCA cells (negative cells). For the normal blood sample, no such cells were detected.

Figure 7:
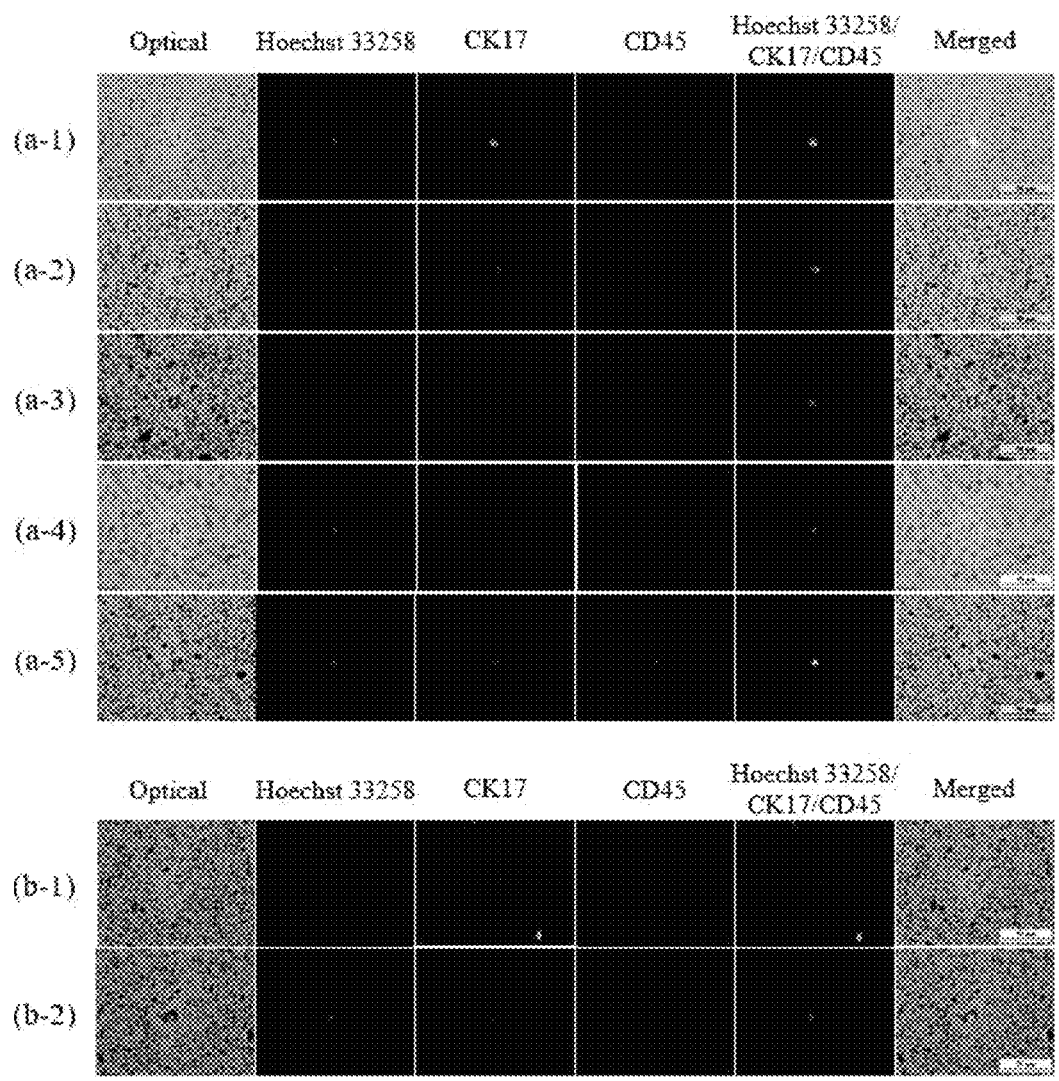
FIG. 7 shows the bright field and fluorescent images of the captured cells detected from blood samples of two patients.

The results of pre-clinical tests have been shown in FIG. 7. All images were captured at 500× magnification. It demonstrates the bright-field and fluorescent images of captured cells detected from blood samples from two patients. FIG. 7 (a-1 to a-4) indicated that four positive cells were discovered in 3 mL blood from the patient (a) who suffers from iCCA, stage 4B. And one negative cell was captured and stained with CD45 Abs, shown in FIG. 7 (a-5). In the blood of Patient (b) suffering from iCCA, one positive and one negative cell was detected, respectively as shown in FIG. 7 (b-1) and (b-2). The results preliminarily proven that the selected octasaccharide SCH-46, specific to Huh28 cells, could be applied on clinical specimens in iCCA. According to fluorescent images, it was verified that SCH-46-coated beads were capable of isolating CCA cells from blood cells with high specificity and affinity. Entire CTC detection procedure also confirmed the applicability in clinical diagnostics.

In summary, the method of the invention has the following effects: the capture rate of cholangiocarcinoma cells is higher than 70%, and the method comprises modifying a surface of a magnetic bead with a variety of octasaccharides with high affinity and specificity to capture and analyze CTCs under test. In addition, compared with the conventional mixer, the method of the invention can reduce the mixing time of the sample to be tested and the specific magnetic beads from 30 minutes to 5 minutes using the microfluidic chip. Through a complete set of the detection process, cholangiocarcinoma cells can be successfully captured for specific fluorescent signals of cholangiocarcinoma showing Hoechst 33258 and cytokeratin 17 (CK17) without anti-CD45 to exclude interference from white blood cells and other cells. Furthermore, compared to the detection time of a conventional CellSearch® machine, the detection time can be reduced to two hours via the application of the microfluidic chip system. The present invention further utilizes a preliminary test outside the chip on a clinical sample, and successfully detects 1 and 4 cholangiocarcinoma cells in 3 mL of blood in two intrahepatic cholangiocarcinoma patients. That is, compared with the prior art, the whole blood volume required by the present invention is only 2-3 mL for the detection of cholangiocarcinoma cells, and the prior art requires at least 7.5 mL of whole blood volume. Therefore, the technical feature of the present invention is to successfully develop an integrated microfluidic system as a method for detecting circulating tumor cells in a small amount for the first time.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for detecting cholangiocarcinoma cells, comprising:
   (a) providing a microfluidic chip, wherein the microfluidic chip consists of an open-type micromixer, a first micropump and a second micropump, a first set of reagent chambers that consists of four reagent chambers and a second set of reagent chambers that consists of four reagent chambers, a supernatant reservoir, a plurality of normally-closed valves, and a waste outlet, wherein the first set of reagent chambers is connected to the first micropump via four normally-closed valves, wherein the second set of reagent chambers is connected to the second micropump via four normally-closed valves, wherein the first and second micropumps are individually connected to the open-type micromixer, wherein the supernatant reservoir is connected to the open-type micromixer, wherein the first set and second set of reagent chambers are arranged symmetrically on opposite sides of the open-type micromixer, wherein the first and second micropumps are arranged symmetrically on opposite sides of the open-type micromixer;
   (b) contacting a sample with a magnetic bead-coated with an octasaccharide which specifically binds cholangiocarcinoma cells via transportation and mixing in the microfluidic chip, wherein the sample is a whole blood from a subject, and the whole blood is subjected to a pretreatment for removing red blood cells and white blood cells; and
   (c) detecting binding of the octasaccharide to the cholangiocarcinoma cells in the sample by immunofluorescence staining on the cholangiocarcinoma cells in the open-type micromixer of the microfluidic chip;
   wherein the cholangiocarcinoma cells are circulating tumor cells in cholangiocarcinoma;
   wherein the microfluidic chip is fabricated with two polydimethylsiloxane (PDMS) layers and a glass substrate; wherein the two PDMS layers include a thick-film PDMS and a thin-film PDMS, the thick-film PDMS is used as an air channel layer, and the thin-film PDMS is used as a liquid channel layer;
   wherein the microfluidic chip operates under a gauge pressure ranging from −400 to −500 mmHg at a driving frequency ranging from 1 to 4 Hz corresponding to a shear force ranging from 27 to 32 nN; and
   wherein the microfluidic chip is set under an incubation time between the magnetic bead modified with the octasaccharide and cholangiocarcinoma cells, and the incubation time is no more than 5 minutes.

2. The method according to claim 1, wherein the cholangiocarcinoma cells are captured by the magnetic bead coated with the octasaccharide, and the cholangiocarcinoma cells bound to the octasaccharide are isolated via a magnetic field.

3. The method according to claim 2, wherein the octasaccharide is attached to a detectable label, and the detectable label is selected from the group consisting of a fluorescent label, a chemiluminescent label, a radioisotope, an enzyme label, and a biotin.

4. The method according to claim 1, wherein the immunofluorescence staining is performed using a cytokeratin 17 (CK17) antibody and a CD45 antibody, and the circulating tumor cells in cholangiocarcinoma are CK17-positive and CD45-negative cells.

5. The method according to claim 1, wherein the octasaccharide has a structural formula (I):

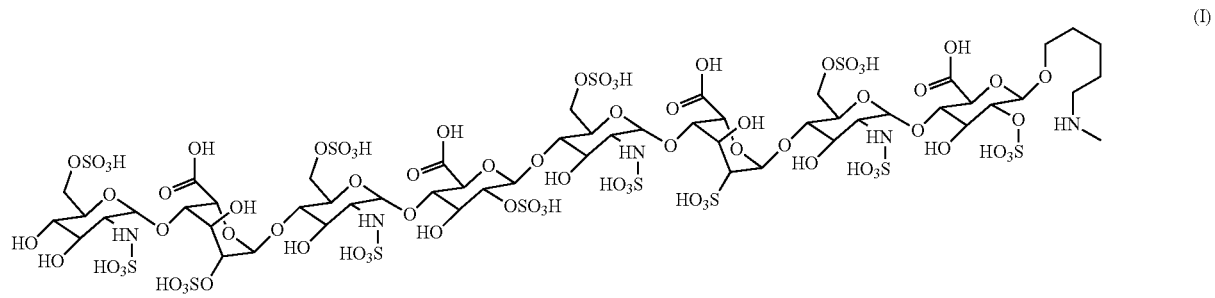

-continued
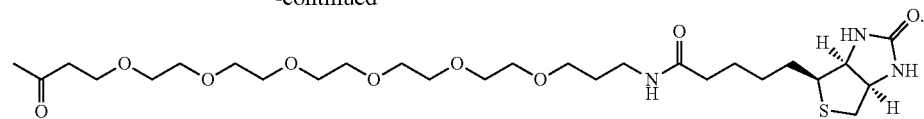
6. The method according to claim 1, wherein the octasaccharide has a structural formula (II):
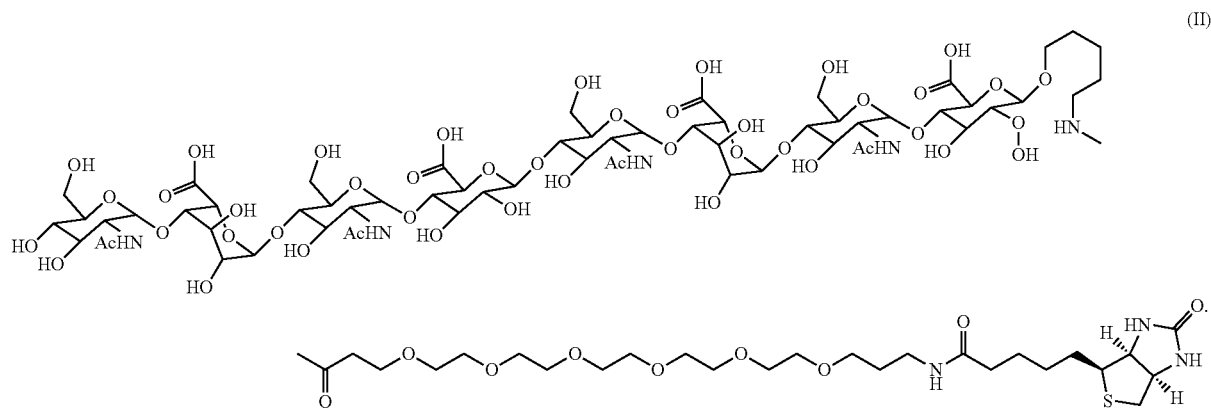
\* \* \* \* \*